United States Patent [19]

Abdulla

[11] 4,398,044
[45] Aug. 9, 1983

[54] SYNTHESIS OF ACETYL-T-ALKANES

[75] Inventor: Riaz F. Abdulla, Greenfield, Ind.

[73] Assignee: Eli Lilly and Company, Indianapolis, Ind.

[21] Appl. No.: 366,881

[22] Filed: Apr. 8, 1982

[51] Int. Cl.$^3$ ............................................. C07C 45/65
[52] U.S. Cl. .................................... 568/318; 568/388
[58] Field of Search .............................. 568/388, 351

[56] References Cited

U.S. PATENT DOCUMENTS 3,609,192  9/1971  Hoffman et al. .................... 568/388

OTHER PUBLICATIONS

House, Modern Synthetic Rxns., pp. 511–513, 552–555 & 624, (1972).
Vigier et al., Chem. Abst., vol. 57, #9798h, (1962).
Robertson et al., Chem Abst., vol. 25, #3324$^8$, (1931).
House and Larson, J. Org. Chem. 33, 61–65, (1968).
Corey and Durst, J. Am. Chem. Soc. 90, 5548–5552, (1968).
Oishi et al., Chem. Pharm. Bull. 17, 2314–2318, (1969).

Primary Examiner—James H. Reamer
Attorney, Agent, or Firm—Joseph A. Jones; Arthur R. Whale

[57] ABSTRACT

Acetyl-tertiary-alkanes are prepared by hydrolytic decarboxylation of tertiary-alkanoylacetonitriles with hydrochloric acid.

18 Claims, No Drawings

SYNTHESIS OF ACETYL-T-ALKANES

BACKGROUND OF THE INVENTION

1. Field of the Invention

This invention belongs to the field of synthetic organic chemistry and provides a process for preparing acetyl-tertiary-alkanes. The compounds are particularly useful as intermediates for preparing a group of 3-alkylpyridazin-6-ylbenzamides which have recently been identified as valuable herbicides. The acetyl-t-alkanes have been difficult to prepare, because of the bulk of the tertiary alkyl group attached to the carbonyl, and the present invention provides a convenient synthesis of these intermediates.

2. State of the Art

Various processes have been used in the art to make acetylalkanes. Corey and Durst, *J. Am. Chem. Soc.* 90, 5548–52 (1968) made acetylcyclohexane and pinacolone by reacting the appropriate ethyl ester with lithium N-(p-tolyl)lithiomethanesulfinamide. House and Larson, *J. Org. Chem.* 33, 61–65 (1968), made acetylheptadecane by reacting the corresponding methyl ester with dimethylsulfone and sodium hydride to obtain the methylsulfonylacetyl intermediate, and reducing off the methylsulfonyl with aluminum amalgam. Phenylacetone, a related compound, was prepared by Oishi et al., *Chem. Pharm. Bull.* 17, 2314–18 (1969), by reacting ethyl phenylacetate with 1-ethoxy-N,N-dimethylvinylamine, deaminating the product on silica gel, and hydrolyzing in hot dilute acid.

SUMMARY OF THE INVENTION

The present invention provides a process for preparing an acetyl-t-alkane of the formula

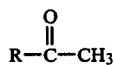

wherein R is of the formula

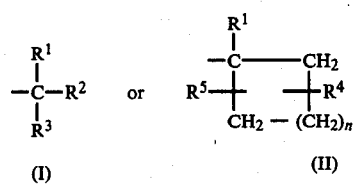

$R^1$ is $C_{1}$–$C_4$ alkyl;

$R^2$ and $R^3$ are independently $C_1$–$C_{13}$ alkyl, or halo-$C_1$–$C_{13}$ alkyl;

n is 0–4;

$R^4$ and $R^5$ are independently hydrogen, halo or $C_1$–$C_4$ alkyl; comprising hydrolytically decarboxylating a t-alkanoylacetonitrile of the formula

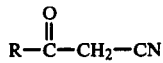

with hydrochloric acid.

DESCRIPTION OF THE PREFERRED EMBODIMENTS

In this document, all temperatures are described in degrees Celsius.

The general chemical names above are used in their ordinary meanings in organic chemistry. Thus, the term $C_1$–$C_4$ alkyl includes such groups as methyl, ethyl, propyl, isopropyl, butyl, s-butyl and t-butyl. $C_1$–$C_{13}$ alkyl includes the groups just mentioned, as well as such larger groups as pentyl, heptyl, undecyl, dodecyl, tridecyl, neopentyl, 1-methylbutyl, 2ethylbutyl, 3-methylbutyl, 4-methylhexyl, 2,2-diethylpentyl, 3-propylhexyl, 1,3-diethylpentyl, 2-methyloctyl, 3-propyloctyl, 4-ethylheptyl, 2-butylheptyl, 3-methyldecyl, 1-ethylundecyl, 2,4-diethylnonyl, 1-pentylhexyl, 5-propyldecyl and the like.

The halo-$C_1$–$C_{13}$ alkyl groups of the compounds prepared by this invention include $C_1$–$C_{13}$ alkyl groups as described above substituted with chlorine, bromine and fluorine atoms in any desired manner, from a single halogen atom on the alkyl group up to and including full halogen substitution. Exemplary haloalkyl groups are further illustrated below.

Similarly, the halogen atoms which may constitute the $R^4$ and $R^5$ substituents of the compounds may be chlorine, bromine or fluorine atoms.

It will be seen that the tertiary alkyl groups of the compounds may be simple groups where the adjacent carbon atom is substituted with 3 alkyl (or haloalkyl) groups, or two of the groups may combine to form a cycloalkyl group, which may optionally be substituted. The cycloalkyl groups may be of from 3 to 7 carbons, as defined by the integer n in the formula above.

Certain categories of the acetyl-t-alkanes constitute preferred products of this invention. The definitions below define the preferred classes of products; it will be understood that various of the definitions may be combined as desired to define further, more limited preferred classes.

A. Compounds of formula I;
B. Compounds of formula I wherein $R^2$ is $C_1$–$C_4$ alkyl or halo-$C_1$–$C_4$ alkyl;
C. Compounds of formula I wherein $R^3$ is $C_1$–$C_4$ alkyl or halo-$C_1$–$C_4$ alkyl;
D. Compounds of formula I wherein $R^2$ is $C_1$–$C_4$ alkyl;
E. Compounds of formula I wherein $R^3$ is $C_1$–$C_4$ alkyl;
F. Compounds of formula I wherein $R^1$ is unbranched;
G. Compounds of formula I wherein $R^2$ is unbranched;
H. Compounds of formula I wherein $R^3$ is unbranched;
I. Compounds of formula II;
J. Compounds of formula II wherein n is 2–4;
K. Compounds of formula II wherein n is 3;
L. Compounds of formula II wherein $R^4$ and $R^5$ are the same;
M. Compounds of formula II wherein $R^4$ and $R^5$ are hydrogen;
N. Compounds of formula II wherein $R^1$ is unbranched.

The products of the process of this invention are further explained by the following group of specific products prepared thereby.

1-acetyl-6,6,6-trifluoro-1-methyl-1-propylhexane
1-acetyl-2-(2,2-dibromoethyl)-1-ethyl-1-methylbutane
1-acetyl-2-fluoro-1-isobutyl-1-isopropyl-3-methylpentane
1-acetyl-1-butyl-3-chloro-1-ethylhexane
1-acetyl-1-s-butyl-3-fluoro-1-pentylheptane 1acetyl-1-(3,3-dichloro-1-ethylbutyl)-1-ethyl-3-methylhexane
1-acetyl-4,5,5-trichloro-2-ethyl-1-(1-ethylpropyl)-1-methylpentane
1-acetyl-1-ethyl-3,3,4-trifluoro-1-hexyloctane
1-acetyl-1-(2-ethylbutyl)-1-isopropyl-4-trifluoromethylheptane
1-acetyl-3-bromo-1-butyl-3-ethyl-1-(1-ethylbutyl)hexane
1-acetyl-9-bromo-1-heptyl-1-methylnonane
1-acetyl-3,3-difluoro-1,5-dimethyl-1-(5-methylhexyl)heptane
1-acetyl-6-chloro-1-(2-ethylpentyl)-1-ethyl-2-propylhexane
1-acetyl-6-bromo-1-isopropyl-1-(1-propylbutyl)decane
1-acetyl-1-t-butyl-10,10,10-trifluoro-1-octyldecane
1-acetyl-5-chloro-1-methyl-2-proply-1-(1-propylpentyl)heptane
1-acetyl-2-butyl-2,3-dichloro-1-(4-ethylhexyl)-1-isopropylhexane
1-acetyl-5,5,6,6-tetrabromo-1-s-butyl-1-(3-methylnonyl)undecane
1-acetyl-1-[4(3-chloropropyl)heptyl]-1-isopropyldecane
1-acetyl-1-(2-butylpentyl)-1-propyl-6-trifluoromethyldecane
1-acetyl-12,12,12-trichloro-1-isopropyl-1-(3-propylhexyl)dodecane
1-acetyl-1-[2-(5,5-dibromopentyl)hexyl]-1-propylundecane
1-acetyl-1-(2-butylhexyl)-7-(2-fluoroethyl)-1-methyldecane
1-acetyl-2-butyl-7,7-dichloro-1-(2,4-diethylhexyl)-1-methyloctane
1-acetyl-2,2-dichloro-1-(1,5-dimethylhexyl)-1-methyltridecane
1-acetyl-1-[4-(3,3,4,4,4-pentafluorobutyl)-octyl]-1-methyldodecane
1-acetyl-8,8,8-trifluoro-1-methyl-2-pentyl-1-(1-pentylhexyl)octane
1-acetyl-14-bromo-1-methyl-1-(2,6-dimethylnonyl)tetradecane
1-acetyl-1-(1,4-dibromo-2,5-diethylnonyl)-1-ethyltridecane
1-acetyl-2-bromo-5-chloro-2-pentyl-1-propyl-1-(2-pentylheptyl)nonane
1-acetyl-1,2,4,8-tetramethyl-1-propyldecane
1-acetyl-1,1-dimethyltetradecane
1-acetyl-2-butyl-1-isobutyl-1-methyldecane
1-acetyl-1,1-diethyl-5-pentylundecane
1-acetyl-11-methyl-1-pentyl-1-propyldodecane
1-acetyl-1-chloromethyl-1-ethyl-3-methylpentane
1-acetyl-1-isobutyl-1-(2-fluoroethyl)-2-ethylbutane
1-acetyl-1-(2,2-dibromopropyl)-1-methylheptane
1-acetyl-1-(4-bromobutyl)-1-t-butyl-3-ethylpentane
1acetyl-1-(1-chloromethylpropyl)-1-ethyl-2-propylbutane
1acetyl-1-pentachloroethyl-1-isopropyloctane
1-acetyl-1-(2,2,3-tribromobutyl)-1-ethyl-6-methylheptane
1-acetyl-1-(5-fluoropentyl)-3-ethyl-1-methylhexane
1-acetyl-1-(2,2-dichloropentyl)-1-methyl-2-propylpentane
1-acetyl-1-(2,2-dibromopropyl)-6,6,6-trifluoro-1-methylhexane
1-acetyl-1-[1-(2,2-dibromoethyl)propyl]-5-bromo-1-ethylpentane
1-acetyl-1-[1-(chloromethyl)propyl]-2-fluoro-1-isopropyl-3-methylpentane
1-acetyl-1-pentachloroethyl-3-chloro-1-propylhexane
1-acetyl-1-(3,4,4-tribromobutyl)-1-s-butyl-3-fluoroheptane
1-acetyl-1-(3,3-dichloro-2-ethylbutyl)-6-fluoro-1-methylhexane
1-acetyl-2,2-dibromo-1-[1-(1,1,2-trichloropropyl)propyl]-1-ethylhexane
1-acetyl-3,3,4-trifluoro-1-methyl-1-octyloctane
1-acetyl-1-methyl-1-(2-propylpentyl)-4-trifluoromethylheptane
1-acetyl-3-bromo-2-ethyl-1-(3-ethylhexyl)-1-methylhexane
1-acetyl-8-bromo-1-methyl-1-(3-methylnonyl)-nonane
1-acetyl-1-(1,1-difluoro-4-methylhexyl)-1-methyldecane
1-acetyl-3-butyl-1-(5-chloro-2-propylpentyl)-1-methylhexane
1-acetyl-6-bromo-1-methyl-1-(3-propylhexyl)-decane
1-acetyl-1-decyl-10,10,10-trifluoro-1-methyldecane
1-acetyl-3-butyl-1-(4-chloro-3-propylhexyl)-1-ethylheptane
1-acetyl-1-(1-butyl-1,4-dichloropentyl)-1,3,5-triethylheptane
1-acetyl-9,9,10,10-tetrabromo-1-(1,3-dimethylhexyl)-1-methylundecane
1-acetyl-1-[3-(2-chloropropyl)heptyl]-1-methyldodecane
1-acetyl-6-trifluoromethyl-1-methyl-1-(1-pentylhexyl)decane
1-acetyl-3,3,4-trichloro-1-methyl-1-(2,6-dimethylnonyl)dodecane
1-acetyl-1-[2-(5-bromopentyl)hexyl]-1-ethyltridecane
1-acetyl-1-ethyl-7-(2-fluoroethyl)-1-(2-pentylheptyl)decane
1-acetyl-1-(1-butyl-4,5-dichloroheptyl)-1-isopropyl-2,3,4-trimethyldecane
1-acetyl-1-(12,12-dichlorododecyl)-1-methyltetradecane
1-acetyl-3-butyl-1-[2-(1,1,2,2-tetrafluorobutyl)octyl]-1-methyldecane
1-acetyl-5-pentyl-1-(2,2,3-trifluoro-1-pentylheptyl)-1-propylundecane
1-acetyl-12-bromo-1-(6-methylundecyl)-1-methyltetradecane
1-acetyl-2,6-dibromo-1-chlormethyl-4,8-diethyl-1-methyldecane
1-acetyl-2-bromo-4-chloro-1-(1-fluoroethyl)-1-methyl-2-pentylnonane
1-acetyl-1,2-dimethylcyclopropane
1-acetyl-3-t-butyl-1-ethyl-2-fluorocyclobutane
1-acetyl-2-chloro-4-ethyl-1-propylcyclopentane
1-acetyl-2-bromo-4-butyl-1-isopropylcyclohexane
1-acetyl-1-butyl-3-methyl-4-isopropylcycloheptane
1-acetyl-1-t-butyl-3-s-butyl-2-ethylcyclopentane
1-acetyl-1-s-butyl-2-isopropyl-3-propylcyclohexane
1-acetyl-1,4-diisobutyl-3-propylcycloheptane
1-acetyl-2-isobutyl-1-methylcyclobutane
1-acetyl-2-bromo-4-s-butyl-1-ethylcyclopentane
1-acetyl-4-butyl-3-chloro-1-ethylcyclohexane
1-acetyl-3-t-butyl-5-fluoro-1-methylcycloheptane The alkanoylacetonitriles which are the starting compounds for the process of this invention are obtained readily by reacting acetonitrile in the presence of sodium hydride with the methyl carboxylate of the acid which provides the desired alkanoyl group. For example, if the R group is to be t-butyl ($R_1$, $R_2$ and $R_3$ are all methyl) the ultimate starting compound is methyl pivalate. The reaction of the methyl ester with acetonitrile is a standard literature method for the preparation of alkanoylacetonitriles such as the starting compounds used in this process.

The synthesis of the acetonitriles is preferably carried out by first suspending sodium hydride in a suitable amount of tetrahydrofuran at ambient temperature, and adding the methyl carboxylate and acetonitrile to the suspension. The mixture is warmed slowly to obtain a gentle reflux, and stirred at that temperature for several hours or overnight. The reaction is an efficient one and produces good yields of the starting compounds. Synthesis of the alkanoylacetonitriles is further explained in the preparations below.

The process of this invention is carried out under mild conditions, and quite unexpectedly produces the desired tertiary acetylalkanes without the undesired rearrangement of the tertiary alkyl groups which would be expected to occur. The rearrangement, properly described as a Wagner-Meerwein rearrangement, is understood to occur in similar reactions in the field of branched alkane chemistry and to be a major problem. See, for example, Banthorpe and Whittaker, *Quart. Revs.* 20, 373 (1966); Dutler et al., *Helv. Chim. Acta.* 38, 1268 (1955); and Brownlie et al., *J. Chem. Soc.* 2419 (1956).

The reagent for the synthesis of this invention is hydrochloric acid. Concentrations in the range of from about 6-normal up to the maximum obtainable concentration (which is about 12-normal) are particularly useful. It is most preferred to use commercial concentrated hydrochloric acid containing about 36–38% by weight of HCl.

When concentrated hydrochloric acid is used, the process of this invention occurs efficiently at temperatures in the range of about 80°–110°, in about 2 hours. The most preferred condition for the process is about the reflux temperature of the reaction mixture, especially when using commercial concentrated hydrochloric acid.

It will be understood that the necessary reaction time will increase markedly when lower temperatures are used, and also when lower concentrations of hydrochloric acid are used. The necessary reaction times are easily identified for each combination of conditions. The optimum time in a given case, of course, is found by a balance between the maximum throughput, obtained by short reaction times, and the maximum yield, obtained by long reaction times.

The products of the present invention are used as intermediates in the synthesis of a series of N-pyridazinylbenzamides which are taught in U.S. patent application Ser. No. 302,323, of Burow. The herbicides are of the formula

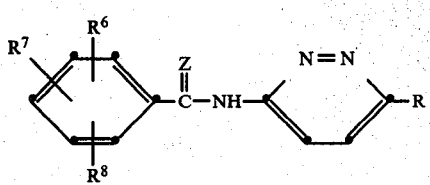

wherein Z is oxygen or sulfur;

$R^6$ is hydrogen, halogen, $C_1$-$C_4$ alkyl, or $C_1$-$C_4$ alkoxy;

$R^7$ hydrogen, halogen, $C_1$-$C_4$ alkyl, $C_1$-$C_4$ alkoxy, $C_1$-$C_4$ alkylthio or trifluoromethyl;

$R^8$ is hydrogen, halogen, $C_1$-$C_4$ alkyl, $C_1$-$C_4$ alkoxy or $C_1$-$C_4$ alkylthio; provided that when one of $R^6$, $R^7$ or $R^8$ is alkyl, one or both of the other phenyl substituents is other than hydrogen; and when $R^7$ is trifluoromethyl, one or both of $R^6$ and $R^8$ is other than hydrogen.

The products of the process of this invention are transformed to the herbicidal benzamides in a simple step-wise process. In the first step, the acetylalkane is reacted with chloral (trichloroacetaldehyde) or its hydrate to obtain a 3-alkanoyl-2-hydroxy compound of the formula

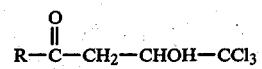

The above intermediate is hydrolyzed with base, preferably in aqueous ethanol, to obtain the corresponding unsaturated acid of the formula

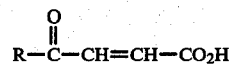

In some preparations the above unsaturated acid is obtained as a mixture with the corresponding keto-hydroxy acid

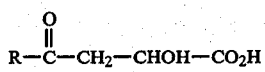

The above acid represents merely incomplete dehydration. The presence of a mixture of this type is not a disadvantage, because the keto-hydroxy acid reacts in the following step just as does the unsaturated acid.

The corresponding pyridazinone is prepared in a process step which is the subject of an application for patent, entitled Synthesis of 6-t-alkyl-3-Pyridazinones, of Riaz F. Abdulla, filed on the same day with this application. The acid is first irradiated with strong light to convert the acid to the corresponding cyclic form,

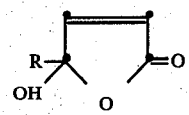

which intermediate is reacted with hydrazine in the presence of ethanol and hydrochloric acid to form the pyridazinone of the formula

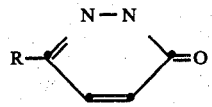

Finally, the pyridazinone is reacted with a chlorinating agent such as phosphorus oxychloride to replace the oxo atom with chlorine, is aminated with ammonia under pressure to prepare the 4-aminopyridazine, and is finally reacted with the appropriate benzoyl (or thiobenzoyl) compound to form the herbicidal benzamide.

Synthesis of the benzamides is further explained in the preparations below.

The benzamide herbicides are used in agriculture as herbicides have often been used in the past. Many of them are so active that application rates in the range of from about 0.1 to about 2 kg. per hectare are adequate. In general, they are used at rates from about 0.05 to about 15 kg. per hectare. When the compounds are used for post-emergence control of weeds, higher application rates, such as from about 1 to about 20 kg. per hectare, are preferred.

It is not necessary to incorporate the herbicides in the soil. The compounds are more potent when incorporated than when applied on the surface of the soil, however, and incorporation is therefore preferred. The compounds are effective when applied either before or after the emergence of weeds; the pre-emergence use of them is more effective and is accordingly preferred. The compounds are effective against a wide range of undesirable vegetation, including most of the herbaceous weeds and grasses which afflict agriculture. Accordingly, the herbicidal benzamides are widely usable.

The benzamides are particularly and notably safe to cereal crops, such as corn, rice and especially wheat, and their use as herbicides in cropland in which such crops are grown is particularly preferred. They may also safely be used, however, in many other crops, such as soybeans, peanuts, cotton, peas and related crops. The compounds are also useful for the control of unwanted vegetation in non-cropland, such as in fallow wheat land and the like. It is often convenient to apply herbicides in combination with other herbicides or with crop protection chemicals such as fungicides, insecticides and the like. The benzamides may conveniently be applied in the form of such combinations when it is desired to do so.

The first preparation below illustrates the synthesis of the alkanoylacetonitriles which are the starting compounds for the process of the present invention.

Preparation 1

(2-ethyl-2-methylbutyryl)acetonitrile

To a suspension of 96 g. of sodium hydride, as a 50% dispersion in mineral oil, in 300 ml. of dry tetrahydrofuran was added, with stirring, 63 g. of acetonitrile and 114 g. of methyl 2-ethyl-2-methylbutyrate. The mixture was then heated gently to 60°–65° and allowed to reflux gently at that temperature overnight. It was then cooled to ice bath temperature, and 2 ml. portions of ethanol were added to decompose the remaining hydride. When the mixture did not foam on further ethanol addition, the mixture was evaporated under vacuum to dryness, and the residue was dumped into 4 liters of water. The aqueous mixture was extracted with hexane to remove the mineral oil, and it was then made acid to pH 2 and was extracted with two 1 liter portions of diethyl ether. The ether was dried over magnesium sulfate and evaporated under vacuum to obtain 122 g. of the desired acetonitrile.

The examples below illustrate the process of this invention.

EXAMPLE 1

1-acetyl-1-ethyl-1-methylpropane

To the 122 g. of alkanoylacetonitrile obtained in Preparation 1 was added 1 liter of 12 N hydrochloric acid. The mixture was heated to reflux, and was stirred under reflux for 2 hours. It was then cooled and extracted with 1 liter of pentane. The organic layer was dried over magnesium sulfate and evaporated under vacuum at 35° to obtain 93 g. of crude product.

EXAMPLE 2

1-acetyl-1-ethylcyclohexane

To 180 g. of (1-ethylcyclohexylcarbonyl)-acetonitrile was added 1 liter of 12 N hydrochloric acid, and the mixture was stirred under reflux for 2.5 hours and was cooled. The mixture was then extracted with one 1000 ml. and one 500 ml. portion of pentane, and the organic layers were combined, dried over magnesium sulfate and concentrated under vacuum at a temperature near 30°. The desired product was found to co-distill, in part, with the solvent, and so the vacuum and temperature were carefully watched to avoid excessive loss of the product, which was identified by its molecular ion in mass spectroscopic analysis, 154. Its boiling point was 44°–45° at 0.4 torr.

The following series of preparations illustrates the manner in which the acetylalkanes prepared by the process of this invention are converted to the herbicidal pyridazinylbenzamides.

Preparation 2

1,1,1-trichloro-5-ethyl-2-hydroxy-5-methyl-4-oxoheptane

A 30 g. portion of the product of Example 1, 1-acetyl-1-ethyl-1-methylpropane, was combined with 38.4 g. of chloral and 36 ml. of acetic acid, and was stirred under reflux, under nitrogen, for 4 days. The solvent was then carefully removed under vacuum to obtain 39 g. of the crude product as an amber, viscous oil.

Preparation 3

5-ethyl-5-methyl-4-oxo-2-heptenoic acid

The product of the preparation immediately above was dissolved in 400 ml. of ethanol and brought to a boil. To it was quickly added 40 g. of potassium hydroxide in 360 ml. of water, and the temperature was held at 72° for 2 minutes. The mixture was then poured immediately into 1 liter of ice-water, and 50 g. of sodium chloride was added. The aqueous mixture was extracted with 1000 ml. of diethyl ether, and the aqueous layer was made acid to pH 1 with concentrated hydrochloric acid. It was then extracted 4 times with 500 ml. portions of dichloromethane, and the organic layers were combined, dried over magnesium sulfate and evaporated under vacuum to obtain 20 g. of the desired acid, as a mixture with 5-ethyl-2-hydroxy-5-methyl-4-oxoheptanoic acid, the presence of which was indicated by nuclear magnetic resonance signals, $\delta 4.35$ (q, 1H); 2.6–3.8 (m, 2H).

Preparation 4

6-(1-ethyl-1-methylpropyl)pyridazine-3-one

The 20 grams of product mixture obtained in Preparation 3 above was added to 200 ml. of ethanol, and 3.6 g. of hydrazine was added. The mixture was stirred under reflux for 3 days, while being irradiated with light from a 300-watt sunlamp. The mixture was in a Pyrex flask, and the lamp was placed 5 cm. from the flask wall. The light emitted by the lamp was primarily of wave length 200–800 m$\mu$. The mixture was then evaporated to an oil under vacuum, and the oil was chromatographed on a 500 g. silica gel column, eluting with 1:1 ethyl acetate:dichloromethane. The product-containing fractions were combined and evaporated under vacuum to obtain a solid residue, which was crystallized from hexane to obtain 4.3 g. of the desired product, m.p. 97°–99°.

Preparation 5

3-chloro-6-(1-ethyl-1-methylpropyl)pyridazine

To 34 g. of 6-(1-ethyl-1-methylpropyl)pyridazin-3-one was added 175 ml. of phosphorus oxychloride, and the mixture was stirred under reflux for 30 minutes. It was then cooled, excess phosphorus oxychloride was removed under vacuum, and the residual oil was poured into ice water. The residue was made basic to pH 9 with ammonia, and triturated. The aqueous mixture so prepared was extracted with two one-liter portions of diethyl ether, and the combined organics were dried and evaporated under vacuum to obtain 35 g. of the desired product, identified by mass spectroscopy, which showed a molecular ion having a weight of 198.

Preparation 6

3-amino-6-(1-ethyl-1-methylpropyl)pyridazine

To the product obtained from the preparation immediately above was added 1000 ml. of liquid ammonia in a pressure vessel, and the mixture was heated at 200° for 50 hours. The mixture was cooled and the volatiles were allowed to evaporate, and the residue was dissolved in 500 ml. of denatured ethanol. The insoluble matter was removed and the solvent was evaporated under vacuum. The residue was purified by chromatography on a 700 g. silica gel column, using ethyl acetate as the eluting solvent. The product-containing fractions were combined and evaporated to obtain an oil which crystallized on standing. The yield was 24 g. of the desired product, m.p. 56°–58° after recrystallization from hexane.

Preparation 7

N-[6-(1-ethyl-1-methylpropyl)pyridazin-3-yl]-2,6-dimethoxybenzamide

A mixture of 21 g. of the product of the preparation immediately above and 23.5 g. of 2,6-dimethoxybenzoyl chloride was dissolved in 500 ml. of benzene, and the mixture was stirred under reflux overnight. The solvent was removed under vacuum, and to the residue was added a solution of 20 g. of potassium hydroxide in 500 ml. of ethanol. The mixture was stirred under reflux for 3 hours, cooled and evaporated under vacuum. To the residue was added 500 ml. of saturated sodium chloride solution, and the aqueous mixture was extracted 3 times with 500 ml. portions of diethyl ether. The organic layers were combined and dried over magnesium sulfate, and the solution was evaporated under vacuum. The crude product was then dissolved in 1000 ml. of diethyl ether and washed with 0.1 N hydrochloric acid. The organic layer was dried and evaporated under vacuum. The oil was treated with 300 ml. of water containing 5 g. of hydroxylamine hydrochloride and 1 liter of diethyl ether, and the 2-phase mixture was stirred for 1 hour. The organic layer was then separated and washed with 2 N sodium hydroxide, dried and evaporated under vacuum to obtain 23 g. of crude product, which was then dissolved in 500 ml. of ethanol containing 40 g. of potassium hydroxide. That mixture was stirred under reflux for 14 hours, cooled and evaporated under vacuum. A 1.5 liter portion of water was added, and the resulting suspension was filtered. The solids were dissolved in ethyl acetate, treated with charcoal and filtered. The filtrate was evaporated under vacuum to obtain a solid which was crystallized from benzene/hexane to obtain the desired product, m.p. 145°–147°.

I claim:

1. a process for preparing an acetyl-t-alkane of the formula

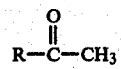

wherein R is of the formula

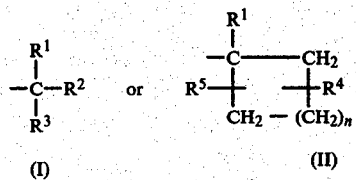

$R^1$ is $C_1$–$C_4$ alkyl;
$R^2$ and $R^3$ are independently $C_1$–$C_{13}$ alkyl, or halo-$C_1$–$C_{13}$ alkyl;
n is 0–4;
$R^4$ and $R^5$ are independently hydrogen, halo or $C_1$–$C_4$ alkyl; comprising hydrolytically decarboxylating a t-alkanoylacetonitrile of the formula

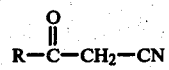

with hydrochloric acid.

2. A process of claim 1 wherein the product is a compound wherein R is of the formula

3. A process of claim 2 wherein the product is a compound wherein $R^2$ is $C_1$–$C_4$ alkyl or halo-$C_1$–$C_4$ alkyl.

4. A process of claim 2 wherein the product is a compound wherein $R^3$ is $C_1$–$C_4$ alkyl or halo-$C_1$–$C_4$ alkyl.

5. A process of claim 3 wherein the product is a compound wherein $R^3$ is $C_1$–$C_4$ alkyl or halo-$C_1$–$C_4$ alkyl.

6. A process of claim 5 wherein the product is a compound wherein $R^2$ and $R^3$ are both $C_1$–$C_4$ alkyl.

7. A process of claim 2 wherein the product is a compound wherein $R^1$ is unbranched.

8. A process of claim 6 wherein the product is a compound wherein $R^1$ is unbranched.

9. A process of claim 8 wherein the product is a compound wherein $R^2$ and $R^3$ are unbranched.

10. A process of claim 2 wherein the product is 1-acetyl-1,1-dimethylethane.

11. A process of claim 2 wherein the product is 1-acetyl-1-ethyl-1-methylpropane.

12. A process of claim 1 wherein the product is a compound wherein R is of the formula

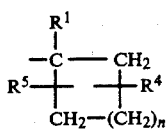 (II)

13. A process of claim 12 wherein the product is a compound wherein n is 2–4.

14. A process of claim 13 wherein $R^4$ and $R^5$ are both hydrogen.

15. A process of claim 12 wherein the product is 1-acetyl-1-ethylcyclohexane.

16. A process of any one of claims 1–15 wherein the concentration of the hydrochloric acid is from about 6 N to about 12 N.

17. A process of claim 16 wherein the concentration of the hydrochloric acid is from about 36% to about 38% by weight.

18. A process of claim 16 wherein the temperature is from about 80° to about 110°.

* * * * *